United States Patent [19]

Nagy et al.

[11] 4,297,892
[45] Nov. 3, 1981

[54] PROCESS AND APPARATUS FOR THE MEASUREMENT OF THE ANISOTROPY VALUE OF FORM CHANGES IN NORMAL DIRECTION IN SHEET METALS

[75] Inventors: Ferenc Nagy; Ferenc Szabó; Zoltán F. Szücs, all of Székesfehérvár, Hungary

[73] Assignee: Magyar Aluminiumipari Tröszt, Budapest, Hungary

[21] Appl. No.: 97,795

[22] Filed: Nov. 27, 1979

[51] Int. Cl.$^3$ ............................................. G01N 3/08
[52] U.S. Cl. ................................................. 73/826
[58] Field of Search .................. 73/826, 789, 794, 760

[56] References Cited

U.S. PATENT DOCUMENTS 2,827,705  3/1958  Elliott et al. .......................... 73/826
3,613,679  10/1971  Bijou .................................... 73/760

FOREIGN PATENT DOCUMENTS 849624  9/1960  United Kingdom ................... 73/826

Primary Examiner—Anthony V. Ciarlante
Attorney, Agent, or Firm—Karl F. Ross

[57] ABSTRACT

The invention concerns a process and an apparatus for measuring the anisotropy value of form changes in normal direction in sheet metals (the r-value). In course of a standard tensile test, the longitudinal change of dimension of the test piece is measured. When a preselected value of change of dimension in longitudinal direction which is characteristic of the material of the test piece, is reacted during the measuring process, the appertaining change of dimension in lateral direction is measured. Thereafter, an r-value is selected from the r-values corresponding to different changes in dimension in lateral direction at a preselected longitudinal change of dimension, which is closest to the one measured at the change of direction in lateral direction. The apparatus comprises comparator and switching units which are connected to signal transmitters converting changes of dimension in longitudinal direction into electric signals. The comparator and switching units compare the electric input signals with reference signals. After the preselected change of dimension in longitudinal direction is reached in the course of the measuring process, these units send an interlocking signal to a further switching and decoding unit. This further switching unit is connected to a comparator unit which compares the electric signals corresponding to changes of dimension in lateral direction with the reference signals.

2 Claims, 2 Drawing Figures

PROCESS AND APPARATUS FOR THE MEASUREMENT OF THE ANISOTROPY VALUE OF FORM CHANGES IN NORMAL DIRECTION IN SHEET METALS

FIELD OF THE INVENTION

The invention concerns a process for the measurement of anisotropy value of form changes in the normal direction of sheet metals. The invention also relates to an apparatus suitable for carrying out the process.

BACKGROUND OF THE INVENTION

The technology of cold forming is widely used in various sections of industry. There is a plurality of known methods (e.g. technological and tensile tests) for the evaluation of the cold-forming properties. In the course of technological tests, the suitability for a particular forming operation can be ascertained.

The recognition that there is a good interrelation between the quotient of the change of dimensions in longitudinal and lateral direction measurable by tensile test was an important step forward. This is the so-called anisotropy in normal direction, i.e. the r value and the result of the deep draw test (cupping) (Lankford, W. T & Associates: Trans.ASM 1950.42, page 1197 and Whiteley R. L. & Associates, Sheet Metal Industries 1961.5 pages 349–353).

The r value can also be used for the determination of the direction of ear formation or earing. The r value characterises the anisotropy of planar form changes of sheet metals because of the relationship:

$$\Delta r = \frac{r_{0°} - r_{90°}}{2} - r_{45°}$$

If the value of $\Delta r$ is positive, the direction of ear formation or earing is inclined to the direction of rolling of the sheet by an angle of 90°; if it is negative, then this angle is 45°. (The subscripts of r in the formula of interrelation mean the angles between the longitudinal direction of test pieces used for the determination of the value of r, and the direction of rolling).

Since, up to the present, there has been no other known characteristic that shows such a good interrelationship of the deep-drawing property of sheet metals, this index number has particular importance in the sorting of sheet metals produced for deep-drawing purposes.

The known processes for measuring the r value can be generally divided into two main groups. In the processes belonging to one of these groups accurate lines are formed in longitudinal and lateral directions on the surface of the test specimens, e.g. by Vickers-pyramids or by photographic methods. Thereafter, the test specimen is stretched by a tensile testing machine to a defined extent and after accurately determining (generally by a highly accurate measuring microscope) the changed length of the measuring lines the r value is obtained by calculation or by nomograms (e.g. Keeler S. P. Machinery 1968.4, pages 94/103).

These processes are labor intensive and unsuitable for measurements carried out in series. Their only advantage is that very little instrumentation is required.

In the processes of the other main group of methods, the longitudinal or lateral form changes of the test piece are continuously registered by electronic tensilometers of high accuracy. The r value is determined either by a suitably programmed digital computer (e.g. Roell-Korthaus Electronic Computer, Sheet Metal Industries 5, pages 450/451), or by a recording co-ordinatograph (e.g. see Hungarian Pat. No. 163,808).

These latter measuring processes eliminate the main drawbacks of the method of the former group. However, their general use is restricted because they require expensive computers or co-ordinatographs and specially trained skilled labor. They are useful therefore primarily in research work, but not the requirements of the material testing in production and application of sheet metals.

OBJECT OF THE INVENTION

The object of the present invention is to provide a process for the determination of the r value on a standard tensile test specimen and simultaneously to determine the usual material properties without disturbing the characteristic.

SUMMARY OF THE INVENTION

The present invention is based on the recognition that at a constantly longitudinal uniform stretching of sheet metal, the r value is the function solely of the lateral change of the dimension. This is clearly shown in the relationship given below. This relationship is obtained by identical transformations of the relative changes of the dimensions contained in the original definition of r value, into absolute changes of dimension respectively by the application of the theorem of the constancy of volume: the lateral change of dimension is expressed by relating it to the longitudinal change of dimension:

$$b = b_o \left[ \left( 1 - \left( 1 + \frac{a}{a_o} \right) \right) \right]^{-\frac{r}{1+r}}$$

wherein $a_o$ and $b_o$ are the initial values of the signalled distance in the longitudinal and lateral directions respectively.

In carrying out the measuring process according to the invention a stage is reached at which point the preselected change of dimension on the standard specimen and the value of the longitudinal change of dimension on the test specimen is reached. The change of dimension in lateral direction is measured and from the values of anisotropy in normal direction corresponding to the changes in dimension in lateral direction the nearest value of anisotropy in normal direction related to the measured lateral dimensional form change is determined.

The apparatus for carrying out the measuring process according to the invention is connected to signal transmitters placed on the standard tensile test piece which convert the longitudinal and lateral dimensional changes of the test piece into electric signals. The signal transmitter is connected to a switching and comparator unit, which compares the changes in dimension in longitudinal direction with corresponding reference signals and if they are either identical with a preselected reference signal or show a difference between them, generate an input signal activating the switching unit. This switching and comparator unit is connected to another switching unit. The output signal of the signal transmitter is coupled to a comparator unit which compares the output signals with reference signals corresponding to anisotropy values appertaining to individual discrete form changes in the normal direction and the output side of this switching unit is connected in series with a decoding unit and with an indicator unit. The suitably stabilized direct voltage required for the individual units of the apparatus is provided by supply units from the mains or from a battery.

The handling of the apparatus is simple and does not require special expertise. The r value is numerically indicated by the apparatus. The determination of the r value does not extend the time required for carrying out a standard tensile test. Pricewise, the apparatus may also have cost advantages for laboratories attached to production lines.

BRIEF DESCRIPTION OF THE DRAWING

The present invention will be further described by way of example only with reference to a preferred embodiment which is illustrated by the accompanying drawing, in which.

SPECIFIC DESCRIPTION

Figure 1:
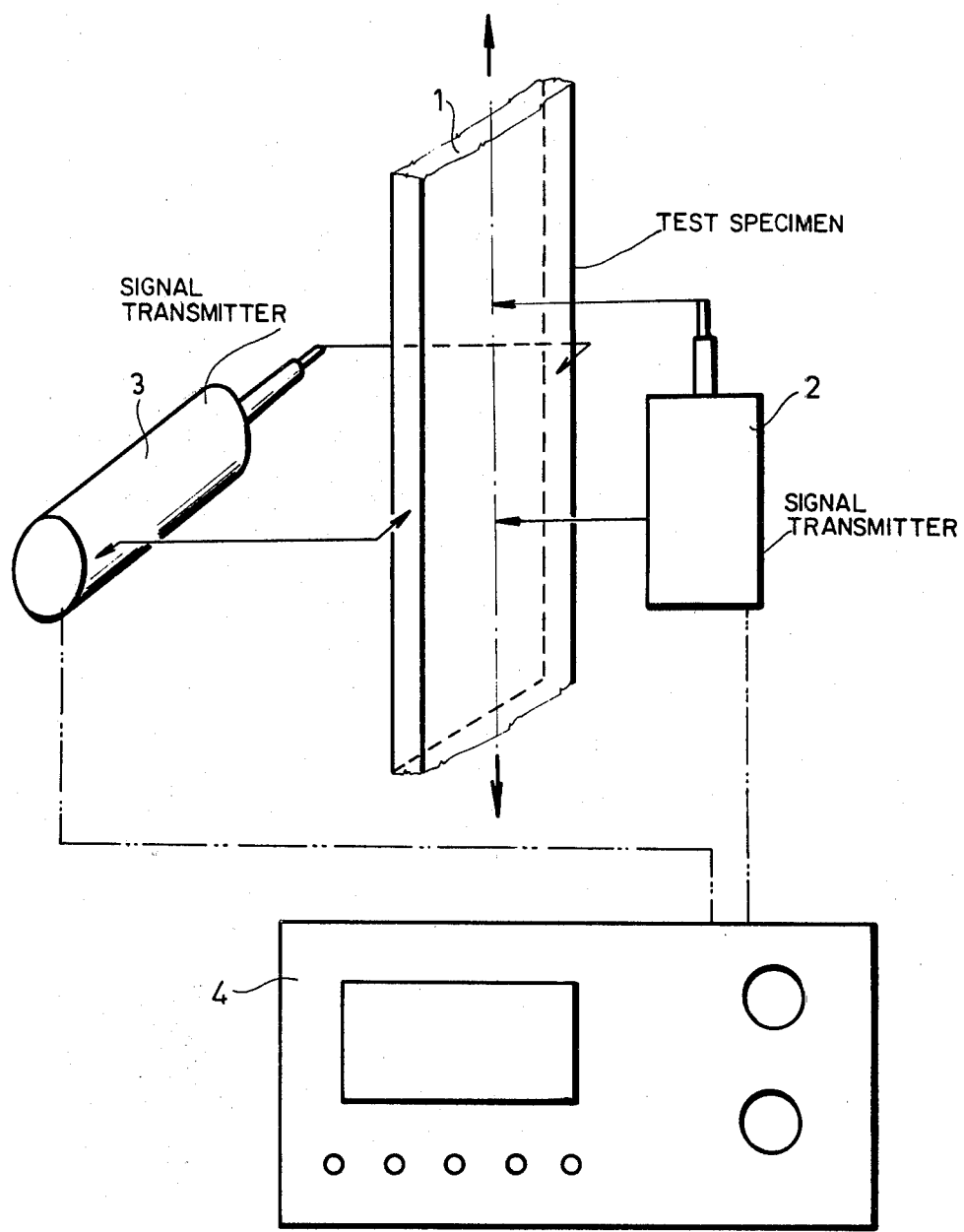
FIG. 1 is a diagram which illustrates the apparatus according to the invention with a signal transmitter placed on the tensile test specimen.
Figure 2:
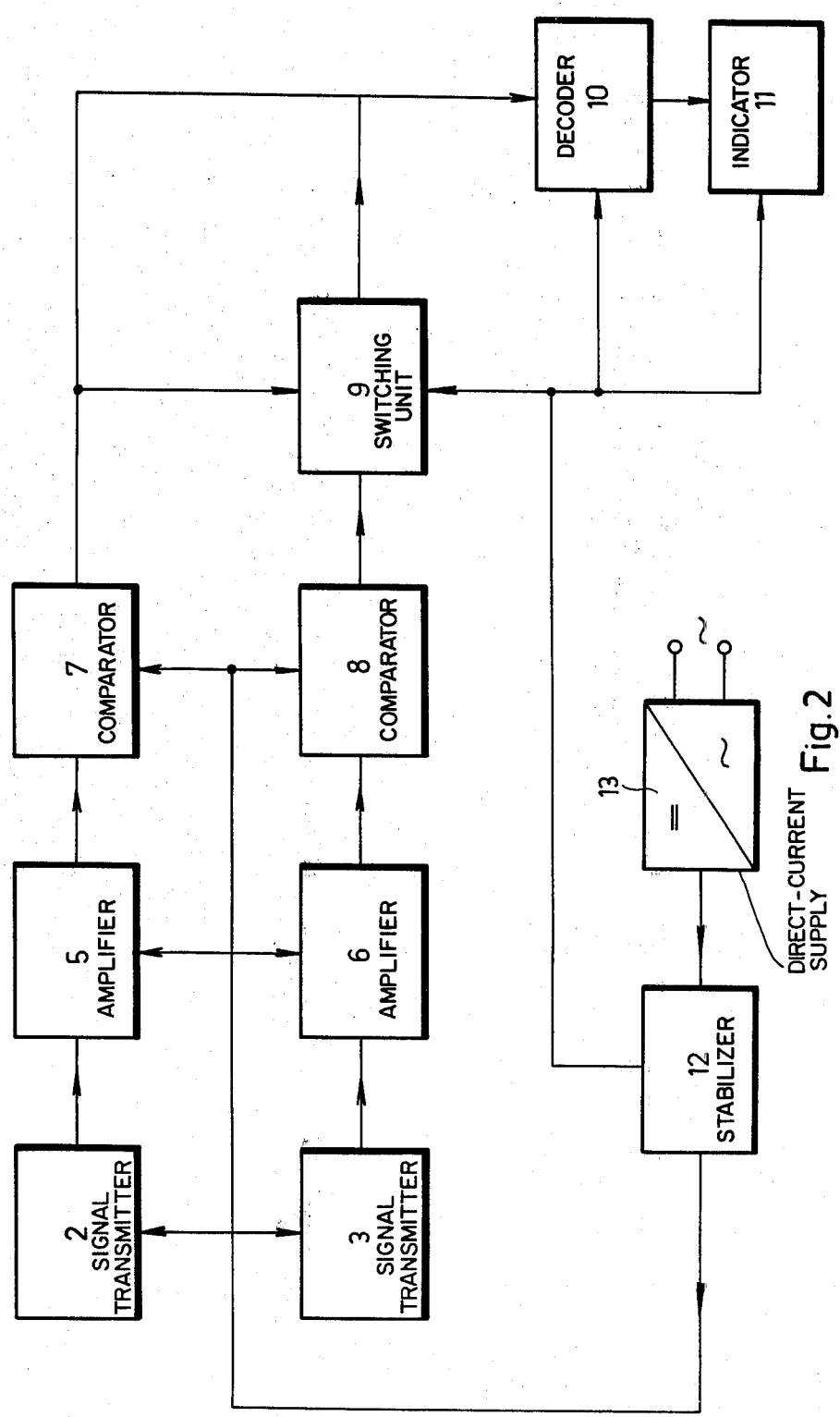
FIG. 2 is a block diagram of the apparatus according to the invention, connected to signal transmitters.

The measurement of the anisotropy i.e. the r value of the form change in normal direction in sheet metals, is carried out simultaneously with the standard tensile test, without disturbing it. The signal transmitter 2 converting longitudinal changes in dimension into an electric signal and the signal transmitter 3 converting lateral changes in dimension into an electric signal are placed on the standard tensile test specimen 1. Signal transmitters 2 and 3 are commercially obtainable e.g. the make of Hewlett-Packard, type DCDT can be individually built signal transmitters measuring displacements and supplying electric signals proportional to the displacements and have a size which permits their fastening to the standard tensile test specimen 1 by means of a suitable gripping attachment. The signal transmitters 2 and 3 are connected to an apparatus 4 according to the invention comprising amplifiers 5 and 6 connected to the signal transmitters 2 and 3. The amplifiers 5 and 6 are one or multistage linear amplifiers containing transistors or integrated circuits, the amplification of which can be varied between wide limits according to the type of signal transmitter used. The input signal is amplified to the required level with a distorion coefficient of less than 0.5%. The amplifier 5 is connected to the comparator and switching unit 7. The unit 7, using semiconductors, generates temperature stabilized direct potential reference signals corresponding to longitudinal changes of dimension. The characteristics of the material being tested are preselectable in advance, for example by means of a push button switch. When the difference between the output signal of amplifier 5 and the selected reference signal is zero, or has a certain defined value by the circuitry, the temperature stabilized trigger circuit with cut off biasing threshold potential transfers an interlock signal to the switching unit 9 and to the decoding unit 10. The trigger circuit generally consists of transistors or integrated circuits (e.g. Schmitt-trigger, comparator etc.) Thus the apparatus does not register further changes of dimension on the test piece 1 once cut off has occurred. The signal transmitter 3 is connected via amplifier 6, to the comparator unit 8. In comparator unit 8, reference signals are generated, for example using a presettable press button, proportional to changes of dimension in the lateral direction belonging to the individual discrete r values according to the change of dimension in longitudinal direction. These reference signals are compared in the comparator unit 8 via amplifier 6, with the electric signals coming from the signal transmitter 3. A reference signal corresponding to the signal coming from the signal transmitter 3 on the output side of the comparator unit 8.

The switching unit 9 comprises temperature stabilized trigger circuits with cut off biasing direct potential, having transistors or integrated circuits. One trigger circuit belongs to each discrete r value, thus only one circuit will trigger during the course of the measurement up to the appearance of the interlocking signal supplied by the unit 7, corresponding to the preselected longitudinal change of dimension. The comparator unit 8 supplies the direct voltage which is necessary for the trigger. Due to the effect of the interlock signal, the measuring apparatus will not register further dimensional changes and will fix the value of r. The expression of the value of r in decimal numerical system is provided by the decoding unit 10 connected to the switching unit 9, comprising suitable gate circuits and SCO decimal decoders. The decoding unit 10 is connected to the indicator unit 11. The indication can be digital or analog. In view of the design of the circuitry, digital indication is preferred which also ensures more accurate readings of values. The required stabilized direct potential for the individual units is supplied by the supply units 12 and 13, which can operate from mains or battery, or expediently by application of integrated circuits.

The apparatus according to the invention indicates the r values with an absolute accuracy of 0.85%. It is advantageous if the r values are determined without using a recording co-ordinatorgraph or a computer.

We claim:

1. A method of determining the anisotropy value in the normal direction, of sheet metals during tensile testing which method comprises measuring the change in dimension in the longitudinal direction for a reference specimen and calculating the corresponding lateral changes in dimension for preselected anisotropy values, measuring the change in lateral dimension in a test specimen for the same predetermined change in dimension in the longitudinal direction as for the reference specimen, and determining the nearest anisotropy value for the test specimen from the measured lateral dimension.

2. Apparatus for determining the anisotropy value changes in the normal direction in sheet metals, which apparatus comprises a signal transmitter to determine and convert longitudinal changes in dimension into electric signals, a signal comparator to accept one or more predetermined reference signals corresponding to predetermined anisotropy values and compare them with signals from the signal transmitter, a switching unit operable by the signal from the signal transmitter, identical with or showing a known difference from one of the predetermined reference signals to pass a signal to a display unit to show the appropriate anisotropy value corresponding to the anisotropy value of the predetermined reference signal which operates the switching unit.

* * * * *